United States Patent [19]

Fife

[11] Patent Number: 5,480,302
[45] Date of Patent: Jan. 2, 1996

[54] ANTI-MICROBIAL APPARATUS AND METHOD FOR DENTAL HANDPIECES

[75] Inventor: Richard K. Fife, Salt Lake City, Utah

[73] Assignee: Gull Laboratories, Inc., Salt Lake City, Utah

[21] Appl. No.: 335,618

[22] Filed: Nov. 7, 1994

Related U.S. Application Data

[63] Continuation of Ser. No. 162,682, Dec. 3, 1993, Pat. No. 5,407,354.

[51] Int. Cl.$^6$ .................................................. A61C 1/16
[52] U.S. Cl. ........................ 433/116; 433/104; 206/438; 206/63.5; 422/20; 422/28; 422/300; 422/307
[58] Field of Search ............................. 433/32, 104, 116; 604/163, 171, 263; 206/363, 364, 368, 369, 438, 439, 63.5; 422/20, 28, 300, 292, 307

[56] References Cited

U.S. PATENT DOCUMENTS

| | | | |
|---|---|---|---|
| 1,485,963 | 3/1924 | Curry . | |
| 1,539,253 | 5/1925 | Fuller . | |
| 1,742,061 | 12/1929 | Curry . | |
| 2,073,137 | 3/1937 | Bimrose | 32/30 |
| 2,997,043 | 8/1961 | Flynn | 206/438 |
| 3,456,780 | 7/1969 | Forman | 206/46 |
| 3,746,201 | 7/1973 | Fujio | 215/38 A |
| 4,178,735 | 12/1979 | Jackson | 206/363 |
| 4,226,935 | 10/1980 | Fusee | 435/14 |
| 4,308,229 | 12/1981 | Voit | 422/28 |
| 4,453,936 | 6/1984 | Cassou | 604/263 |
| 4,460,820 | 7/1984 | Matsumoto et al. | 219/385 |
| 4,495,903 | 10/1984 | Steenhuisen et al. | 604/111 |
| 4,619,645 | 10/1986 | Hussey | 604/111 |
| 4,728,290 | 3/1988 | Eisner et al. | 433/116 |
| 4,752,444 | 6/1988 | Bowen et al. | 422/28 |
| 5,137,689 | 8/1992 | Cantrell | 422/28 |
| 5,217,370 | 6/1993 | Craig et al. | 439/116 |

FOREIGN PATENT DOCUMENTS

| | | |
|---|---|---|
| 248188 | 2/1992 | United Kingdom . |
| 2251382 | 7/1992 | United Kingdom . |
| WO9203171 | 3/1992 | WIPO . |
| 2003171 | 3/1992 | WIPO ........................ 422/28 |

OTHER PUBLICATIONS

Article dated Jul./Aug. 1992 entitled Infection Control 92 Report.
Article in Trends in Dentistry entitled Dentists' Answering Call for Handpiece Sterilization (date unknown).

(List continued on next page.)

*Primary Examiner*—Cary E. O'Connor
*Attorney, Agent, or Firm*—Foster & Foster; Lynn G. Foster

[57] ABSTRACT

A multiple stage anti-microbial apparatus and methods are disclosed, which provide capacity to process a handpiece between patients including soaking, de-overburdening via use of ultrasonic energy, treating with exposing to anti-microbial heat, accommodating coordinated though separate autoclaving, and accommodating contiguously packaging in a heat shrunk sheath after multiple anti-microbial treatment to prevent later contamination through the air. The distal portion of the heat shrunk sheath is initially removed along weakened paths to expose the operative head of the handpiece, accommodating grasping of the handpiece handle through the remainder of the sheath during use of the handpiece on the patient. After such use, the remainder of the sheath is removed along a weakened path and discarded.

The anti-microbial apparatus comprises a portable casing with one or more exterior lids or covers. An ultrasonic basin provides a bath for soaking, liquid anti-microbial activity and removal of debris. A heat chamber accommodates facile manual introduction and movement therein of the distal end and a substantial portion of the handle of the handpiece, following the bath treatment, to dry and expose the handpiece to anti-microbial heat and anti-contamination sheath upon the handpiece.

6 Claims, 7 Drawing Sheets

OTHER PUBLICATIONS

Article in Trends in Dentistry dated Dec. 1991 entitled Awareness of Instrument Disinfection and Sterilization Needs Attains New Levels.Article in Dental Products Report, entitled Handpiece Asepsis (date unknown).
Infection Control 93 Report dated Sep. 1993.
Article dated Oct. 1992, entitled Is Your Dentist Taking the Best AIDS Precautions?.
Article in The Salt Lake Tribune dated Jan. 7, 1992, entitled Dentist with AIDS Points to Need for Overhaul of CDC Guidelines.
Article in ASM News dated Jan. 2, 1991, entitled Risk of Infection From Dental Handpieces.
Article emitted How to Control Infection Risks in Dental Office (date unknown).
Article in American Dental Association News dated Aug. 17, 1987, entitled OSHA to Police Infection Control.
Undated article entitled Health–Care Workers Warned all Patients May Carry AIDS.
Undated article emitled Infection Control: Fact and Reality.
Article in Standard Examiner dated Apr. 18, 1993, entitled Dentists Biting Down on Bacteria.
Infection Control 88 Report, dated Mar. 1988.
Literature from Worldwide Environmental Pollution Control Specialists on Sporicidin Disinfectant Solution.
Pp. 105, 258, and 259 listing surgical/sundry supplies.
Article entitled The Ultimate Ultrasonic Cleaning System.
Pp. 76, 77, and 229 listing equipment and supplies.
Literature from Health–Sonics Corporation on Ultrasonic Cleaning Units, Accessories and Asepsis Products.
Literature from Viro Research International, Inc. on VIRONOX–9.
Advertisment for an IMS cassette system and Bransonic ultrasonic tabletop cleaner by Branson Ultrasonics Corporation.
Comparative Data on Multicide Plus from Biotrol International.
Comparative Data on Biocide from Biotrol International.
Coupons for Asept–All Antimicrobial Hand Soap, Pro–Portion Unit Dose Ultrasonic Cleaner, and Purevac Evacuation System Cleaner.
Article from Branson Ultrasonic Corporation on Aqueous Ultrasonic Cleaning.
Article from Carroll Chemical Specialties on Carroll QUAT 9.0.
Article on K. O. Dyne.
Surge Material Safety Data Sheet.
Article from Weber Valley Dental Supply on Chlorostat.
Article in Clinical by Dr. R. R. Runnells entitled Visible Gloves Halt Office Cross–Infection (date unknown).
Article in Military Medicine, vol. 156, dated Jan. 1991, entitled Infection Control of Field Dental Units.
Testing results.
Protectoral Features.
Operating Manual for Protectoral from Gull Medical.
Article from Gull Laboratories, Inc. on Protectoral Multi–Wash.
Article from Gull Laboratories, Inc. on Protectoral Multi–Wash Spray.
Article from Gull Laboratories, Inc. on Protectoral Multi–Wash Concentrate.
Article on Multi–Wash.
Article in Journal HSPD by Howard Jamner entitled Care and Handling of Surgical Instruments.
Technical Bulletin B–103 from Viro Research International, Inc.— Virucidal Activity of Nonoxynol–9.
Article in Dental Clinics of North America, vol. 35, No. 2, dated Apr. 1991, entitled Role of Disinfectants in Infection Control by John A. Molinari, Ph.D. and R. R. Runnells, DDS.
Sterlization, Disinfection, and Antisepsis in the Hospital by Martin S. Favero and Walter W. Bond.
Article in Dental Products Report entitled Infection Control 92 Report, dated Oct. 1992.
Article in Dental Clinics of North America, vol. 35, No. 2, dated Apr. 1991, entitled Hazardous Waste Management by Milton E. Schaefer, DDS, MLA, FACD.
Final Report submitted by Epidemiology and Disease Control Program on Potential Human Immunodeficiency Virus Transmission via Medical Devices.
Technical Bulletin A–103 by Viro Research International, Inc.— Antimicrobial Effects of Parachlorometaxylenol.
Literature from Biotrol International on BANIQUE 3.
Pp. 11 and 12, descriptions of Multi–purpose UltraSonic Cleaner Solution, Skin Lotion with Vitamin E, Lotion Cleanser, and Derm–Aseptic Cleanser 3% PCMX.
Rebate coupons for Pro–Portion Unit Dose Ultrasonic Cleaner and Asept– All Antimicrobial Hand Soap.
Advertisement for Vacusol Atomizer.
Pp. 94 and 95, Disinfection and Sterilization Supplies.
Advertisement for Omnicide by Healthco Specials.
Advertisement for Sporicidin.
Advertisement from Nevin Laboratories, Inc. for Decident.
Advertisement—Quality Johnson & Johnson Products.
P. 81—Pinnacle Innovative Infection Control Products.
P. 100—Free Product Offers From 3M.
P. 105—Specials From Healthco.
P. 82—Healthco Professional Hand Care System.
P. 83—Advertisement for Bactoshield.
Advertisement for Liquid Dial—Germ Free Hands in 2 Easy Steps.
List of Disinfectants by Chemical Group.
Disinfectants—ADA/CDC Accepted.
Chemical Group Ideal Disinfectant Rating Chart.
Product list for surgical/sundry supplies.
Article by A. Joanne Bednarz–Prashad and Raymond M. G. Boucher entitled Synergistic Virucidal Effects of Ultrasonics and Acid Glutarldehyde, dated Nov./Dec. 1982.
Article in Journal of Clinical Microbiology, May 1976, pp. 474–479, entitled Effect of Sonic Treatment on Pure Cultures and Aggregates of Bacteria.
Article in Nature vol. 267, dated May 12, 1977, emitled Cellular Inactivation by Ultrasound.
Article by R. M. G. Boucher, Ph.D. dated May 23, 1978, entitled Ultrasonics— A Tool to Improve Biocidal Efficacy of Sterilants or Disinfectants in Hospital and Dental Practice.
Article in Hospital Topics, dated Apr. 1966, entitled Sonication–Germicide Treatment in Surgical Instrument Cleaning by Ralph A. Slepecky, Ph.D.
Article dated Oct. 1982, by John A. Molinari, Ph.D., MaLcolm D. Campbell, B. A., D.D.S., and Jane York, R.D.H., M.A., entitled Minimizing Potential Infections in the Dental Practice.
Article in The Guthrie Bulletin, dated Summer 1978 by William C. Beck, M.D., F.A.C.S., entitled Sterilization by a New Technique—Ultrasonic Plus Chemicidal Action (Biocide).
Article in the Journal of Denistry for Children, dated Jan.–Feb. 1970, entitled Ultrasonics and Benzalkonium Chloride as a Method of Sterlizing Dental Instruments by Brad Perkulis, D.D.S., M.S., Warren E. Engelhard, Ph.D., and William S. Kramer, D.D.S., M.S.

Specifications of IGEPAL CO–630 (Nonionic) by GAF Corp.

Article by Samuel S. Asculal, Margaret T. Weis, Martha W. Rancourt, and A. B. Kupferberg, dated Sep. 15, 1977, entitled Inactivation of Herpes Simplex Viruses by Nonionic Surfactants.

Article in the Journal of the Mighican Dental Association by Virginia A. Merchant, MD, DMD, Michael J. Gleason, PhD, DDS, and John A. Molinari, PhD, entitled Infection Control Practices in Michigan Dental Offices; Report of a Survey.

Article by the American Dental Association, dated Aug. 1992, entitled Infection Control Recommendation.

Article in Dental Clinics of North America, vol. 34, No. 1, Jan. 1990, entitled Controversies in Infection Control by John A. Molinari, PhD., Virginia A. Merchant, MD, DMD, and Michael J. Gleason, PhD, DDS.

Article in The Lancet, dated Sep. 28, 1985, emitled Resistance of AIDS Virus at Room Temperature.

Article in The Lancet, dated Dec. 28, 1985, entitled Inactivation of HTLV– III/LAV–Infected Cultures of Normal Human Lymphocytes by Nonoxynol-9 In Vitro.

Article reprinted from American Laboratory, dated Oct. 1975, entitled Ultrasonic Disruption by Howard Alliger.

Article by MAJ Michael F. McCarthy, DC USA entitled Infection Control of Field Dental Units.

Article in JADA, vol. 123, dated Mar. 1992, entitled How Infection Control Procedures Are Affecting Dental Practice Today by Kent D. Nash, Ph.D.

Article in Dental Clinics of North America, vol. 35, No. 2, dated Apr. 1991, entitled Environmental Barriers in Dental Office Infection Control by Robert J. Whitacre, MD, DDS.

Article in General Dentistry dated May–Jun. 1987, entitled Comparison of Dental Surface Disinfectants by John A. Molinari, PhD, Michael J. Gleason, PhD, DDS, James A. Cottone, DMD, MS, FAGD, and Edward D. Barrett, MD, DDS, MAGD.

Article in JADA, vol. 117, dated Jul. 1988, entitled Cleaning and Disinfectant Properties of Dental Surface Disinfectants by John A. Molinari, PhD, Michael J. Gleason, PhD, DDS, Jamse A. Cottone, DMD, MS, and Edward D. Barrett, MS, DDS.

Article by John A. Molinari, PhD, Malcolm D. Campbell, BA, DDS, and Jane York, RDH, MA, dated Oct. 1982, entitled Minimizing Potential Infections in Dental Practice.

Article in Dental Clinics of North America, vol. 35, No. 2, dated Apr. 1991, entitled Infection Control of In–Office Dental Laboratories by Arlo H. King, MSgt, USAF, CDT, and Bruce Matis, Col, USAF, DDS, MSD.

Literature dated Feb. 15, 1992, on Sonicator Ultrasonic Processors.

Literature from Heat Systems Ultrasonics on Sonicator Series Application Notes.

Literature from Infection Control Devices Branch, Division of General and Restorative Devices, Office of Device Evaluation, dated Jan. 31, 1992, entitled Guidance on the Content and Format of Premarket Notification (510(k)) Submissions for Liquid Chemical Germicides.

Article in the British Dental Journal, dated Oct 25, 1991, entitled Compliance with Infection Control Procedures in a Dental Hospital Clinic by C. Scully, MD, PhD, MDS, FDS, MRCPath, and S. R. Porter, PhD, BSc, MBChB, FDS.

Article in JADA, vol. 122, dated Oct. 1991, entitled Effectiveness of Dental Office Instrument Sterilization Procedures by Richard H. Hastreiter, DDS, MPH, John A. Molinari, PhD, Myron C. Falkden, MS, MPH, PhD, Mildred H. Roesch, RDH, MPH, Michael J. Gleason, PhD, DDS, Virginia A. Merchant, MD, DMD.

Article in Journal of Parenteral Science and Technology, vol. 40, No. 31, dated May–Jun. 1986, entitled Parenteral Fundamentals.

Two–page list of ADA Accepted Products.

Article by Viro Research International, Inc. entitled Technical Bulletin.

Pp. 128–133 of Factors Influencing the Efficacy of Antimicrobial Agents.

P. 126—Article on Neutralisation of Antimicrobial Agent.

Pp. 141–121—Article on Concentration of Antimicrobial Agent.

Pp. 122–125—Factors Influencing the Efficacy of Antimicrobial Agents.

Pp. 94–106—Types of Antimicrobial Agents.

Pp. 42–47—Types of Antimicrobial Agents.

Final Report from Indiana University, School of Dentistry, Departmene of Oral Microbiology, dated Aug. 2, 1989.

Pp. 32–38—Performance Criteria.

Chapter 13—Heat Sterilisation.

Chapter 13, pages 454—464, Destruction of Bacterial Spores by Thermal Methods.

Pp. 445–451, Heat Sterilisation.

Article in Ultrasonics, dated Jul. 1967, entitled Sonochemical Sterilization by R. M. G. Boucher, M. A. Pisano, G. Tortora, and E. Sawicki.

Article in Applied Microbiology, dated Aug. 1971, pages 160–164, entitled Ultrasonic Synergistic Effects in Liquid–Phase Chemical Sterilization by Gonzalo Sierra and Raymond M. G. Boucher.

Article in Applied Microbiology, dated Nov. 1967, pages 1257–1261 entitled Synergistic Effects in Sonochemical Sterilization by Ramond M. G. Boucher, Michael A. Pisano, George Tortora, and Edward Sawicki.

Article by Edwin A. Pecker, emitled Ultrasonic Sterilization.

Article in Oct. 12, 1934, issue of Science, emitled A Constant Rate Dropping Device for Liquids.

Article in May 4, 1934, issue of Science, entitled The Virucidal Action of High Frequency Sound Radiation.

Article dated Feb. 27, 1937, entitled Effect of Intense Sonic Vibrations on Elementary Bodies of Vaccinia by Thomas M. Rivers, MD, Joseph E. Smadel, MD, and Leslie A. Chambers, PhD.

Literature on Hydrion Sanitizer.

Evaluation of Useful Antimicrobial Chemicals.

Article in JADA, vol. 116, dated Feb. 1988, entitled Infection Control Recommendations for the Dental Office and the Dental Laboratory.

Five pages from Chapter 2—Types of Antimicrobial Agents.

Comparison of Dental Surface Disinfectants by John A. Mulinari, PhD, Michael J. Gleason, PhD, DDS, James A. Cottone, MDM, MS, FAGD, and Edward E. Barrett, MS, DDS, MAGD.

Protectoral Reference List—Component Use Research.

Letters to the Editor, JADA, vol. 120, dated Jan. 1990.

Article in JADA, vol. 119, dated Oct. 1989, entitled Antimicrobial Activity of Environmental Surface Disinfectants in the Absence of Presence of Bioburden by Rella P. Christensen, PhD, Richard A. Robison, PhD, Daena F. Robinson, BS, Brad J. Ploeger, BS, Ronald W. Leavitt, PhD, and Howard L. Bodily, PhD.

Article by ADA, entitled Infection Control: Fact and Reality.

Pp. 157–166, Annals New York Academy of Sciences, Article entitled AN Assissment of the Airborne Route in Hepatitis B Transmission by Norman J. Petersen.

Article in Infectious Disease Clinics of North America, vol. 3, No. 4, dated Dec. 1989, entitled Risks to Health Care Workers From Occupational Exposure to Hepatitis B Virus, Human Immunodeficiency Virus, and Cytomegalovirus by Julie Louise Gerbercling, M. D.

Article in JADA vol. 99, dated Sep. 1979, entitled Air Sampling for Hepatitis B Surface Antigen in a Dental Operatory by Norman J. Petersen, S. M., Walter W. Bond, MS, and Martin S. Favero, PhD.

Article by Earl R. Kern entitled Preclinical Evaluation of Antiviral Agents: In Vitro and Animal Model Testing.

Article in The Journal of Prosthetic Dentistry by R. R. Runnells, DDS, entitled An Overview of Infection Control in Dental Practice.

Infection Control 91 Report, dated Sep. 1991.

Article in Applied Microbiology, dated Sep. 1966, entitled Sterilizing Effects of High–Intensity Airborne Sonic and Ultrasonic Waves by Michael A. Pisano, Raymond M. G. Boucher, and I. Edward Alcamo.

Sales Meeting 1990—Equipment Sterilization Options in the 90's by Darryl Peterson.

Article dated Nov. 30, 1992, by F–D–C Reports, Inc. on Oralsafe, Inc. Selling Oralsafe Disposable Dental Handpiece.

Article in Medical Device and Diagonstic Industry entitled Applying Hazard Analysis to Medical Devices, Part II: Detailed Hazard Analysis by Bill J. Wood and Julia W. Ermes.

Advertisement for Vital Defense by Block Drug Corporation, dated Sep. 1993.

Pp. 88–91 from Dental Products Report—1993 Recommendations for Infection Control Practices in Dentistry.

Protectoral Sheath System Testing—2 pages.

Pp. Pages 412 and 415 of the Journal of the Michigan Dental Association, vol. 64, dated Oct. 1982.

Article in General Dentristry dated May–Jun. 1987, entitled Comparison of Dental Surface Disinfectants by John A. Molinari, PhD, Michael J. Gleason, PhD, DDS, James A. Cottone, DMD, MS, MAGD, and Edward D. Barrett, MS, DDS, MAGD.

Letters to the Editor, JADA, vol. 118, dated Mar. 1989.

Article in General Dentistry dated Jan.–Feb. 1989, entitled Infection Control in Prosthodontics: A Choice No Longer by Virginia A. Merchant, MS, DMD, and John A. Molinari, PhD.

Article entitled Considering a Dental Computer?.

Article by Milton E. Schaefer, DDS, emitled Infection Control in Dental Laboratory Procedures.

Vol. 15, No. 1, pp. 1–16—Hospital Infection Control, dated Jan. 1988.

Literature from Health–Sonics Corporation on Ultrasonic Cleaning Units, Accessories and Asepsis Products.

Article in JADA, vol. 117, dated Aug. 1988, entitled Infection Control Procedures and Products: Cautions and Common Sense.

P. 283—Microbiology/Immunology.

Pp. 99–117 of The American Journal of Infection Control, vol. 18, No. 2, dated Apr. 1990.

Guidelines for the Premarket Testing and Labeling of Antimicrobial Agents for Medical Devices by Center for Devices and Radiological Health, Food and Drug Administration, dated Nov. 18, 1986.

Sales and Registration Guide.

Toxicological Data Summary.

Material Safety Data Sheet by GAF Chemicals Corporation.

Advertisement for Multi–Purpose Ultra Sonic Cleaner Solution by Health Sonics.

Directions for use of Multi–Wash.

Product Introduction—Protectoral.

ANTI-MICROBIAL APPARATUS AND METHOD FOR DENTAL HANDPIECES

CONTINUITY

This application is a continuation of my U.S. patent application Ser. No. 08/162,682, filed Dec. 3, 1993, now U.S. Pat. No. 5,407,354.

FIELD OF INVENTION

The present invention relates generally to dental handpieces and more specifically to anti-microbial apparatus and methods for treating dental handpieces.

BACKGROUND

Prevention of contamination and cross-contamination have long been matters of primary concern in the dental/medical field. Where handpiece instruments must be reused on successive patients care is required as are certain anti-microbial steps to prevent transmission of virally or bacterially caused infections from one patient to another. An equal concern is to obviate transmission of such infections from or to the health care provider.

An increasing awareness of the potential for the spread of highly contagious viral and bacterial diseases has led to further emphasis being placed on infection control in the dental operatory. The American Dental Association (ADA) and the Centers for Disease Control (CDC) have been instrumental in publishing guidelines intended to reduce the opportunity for disease transmission during the practice of dentistry. These recommendations support the use of protective apparel by dental professionals whose ordinary duties require hands-on contact with patient body fluids, instrumentation and materials used in dental procedures. It is also recommended that non-disposable instrumentation and materials used in the dental operatory be at least disinfected.

"Sterilization" is the process by which micro-organisms are destroyed, including viruses, bacteria, fungi, and spores. Sterilization may be achieved by (1) steam under pressure (autoclave), (2) prolonged dry heat, (3) chemical vapor, (4) ethylene oxide gas, and (5) submersion in chemical sterilants. "Disinfection" is less lethal to microbials than sterilization and typically requires application of a chemical registered with the EPA.

The ADA has recommended that high-quality disposable medical gloves, a surgical mask covering the nose and mouth, and protective eye wear be worn by dental professionals due to constant exposure to patient-contaminated coolant aerosols associated with high speed handpieces as well as exudates of blood, pus, saliva, oral tissue, and decayed tooth material. It is recommended that the dental assistant and the hygienist wear disposable medical gloves. Hand washing and use of oral rinses, a rubber dam, and a saliva evacuation system are also encouraged. Training each health care provider is also important.

The ADA has also recommended autoclaving for instruments and non-disposable materials that are able to withstand the high heat of an autoclave cycle. Non-autoclavable instrumentation and materials should be chemically disinfected with a properly diluted, and freshly prepared disinfectant solution according to the manufacturer's instructions. Large equipment in the dentists' office should be "wiped down" routinely with a suitable anti-microbial solution. Significantly, hepatitis B and HIV are heat sensitive viruses, which are essentially rendered non-contagious by short-term autoclaving.

Except for a suggestion of wiping the handpiece routinely with recommended "wipe down" disinfectants, there is, to our knowledge, no other ADA recommended technique for the disinfection of heat intolerant handpieces between patients. And yet, the handpiece is subjected to the exact same patient-contaminated coolant aerosols and exudates as are the dentist's hands, nose and mouth, and eyes. The handpiece is not only subjected to the contaminated material cast onto it by the coolant aerosol and the mechanical rotation of the tool, but also contaminants transferred to the handpiece by the dentist's glove. Thus, a potential source of cross-contamination from patient to patient exists through the handpieces and microbial contaminants surviving the disinfectant wipe are likely to be transferred to subsequent patients on the newly-donned gloves of the dental professional. Handpieces in today's technology have turbine blades which spin at more or less 500,000 revolutions per minute under air pressure. When the air and/or water pressures are turned off, a vacuum is created which may suck blood, saliva, and serum into the handpiece as a potential source for cross-contamination.

Transmission of microbials through the air in dental offices is also a matter of substantial concern.

Diseases of concern comprise the common cold, hepatitis B (HBV), non-A/non-B hepatitis, influenza, measles (German and rubeola), tuberculosis, staphylococcus, and streptococcus, herpes infections including chicken pox, infectious mononucleosis, epstein bar, herpetic whirlow, herpetic conjunctivitis, and AIDS (the HIV [human immunodeficiency virus] virus).

While it is clear that autoclave sterilization is the anti-microbial treatment of choice, the cost of buying, operating, and maintaining autoclave equipment is high and more handpieces need to be purchased and utilized where handpiece autoclaving occurs between each patient. Also, as stated above, not all handpieces can withstand the heat of autoclaving. Thus, many doctors today, however, appear to find it impractical to sterilize handpieces after each patient use because of possible damage to the devices and the necessary burdensome financial investment in multiple handpieces required to maintain an acceptable instrument flow. Nevertheless, the CDC currently recommends heat treatment of all handpieces using also acceptable methods which assure internal and external sterility between patients.

BRIEF SUMMARY AND OBJECTS OF THE PRESENT INVENTION

In brief summary, the present invention is intended to alleviate the above-mentioned problems of the prior art. The present invention comprises a multiple stage anti-microbial apparatus and methods are provided which significantly address the contamination and cross-contamination problems mentioned above. The present invention provides the capacity to process a handpiece between patients including soaking, de-overburdening via use of ultrasonic energy, treating with exposing to anti-microbial heat, accommodating coordinated though separate autoclaving, and accommodating contiguously packaging in a heat shrunk sheath after multiple anti-microbial treatment to prevent later contamination through the air. The sheath may be manually severed and removed immediately prior to use on an ensuing patient. Preferably, only a distal portion of the sheath is initially removed along weakened path to expose the operative head of the handpiece, accommodating grasping of the handpiece handle through the remainder of the sheath during use of the handpiece on the patient. After such use, the remainder of the sheath is removed along a weakened path and discarded.

The apparatus is relatively inexpensive, but efficacious as a microbial deterrent. In its preferred form, the anti-microbial apparatus comprises a portable casing with one or more covers. An ultrasonic basin provides a bath for soaking, liquid anti-microbial activity and removal of debris. A heat chamber accommodates facile manual introduction and movement therein of the distal end and a substantial portion of the handle of the handpiece, following the bath treatment, to dry and expose the handpiece to anti-microbial heat and anti-contamination sheath upon the handpiece. The preferred apparatus is without water or drain connections, depending only on household electricity and equipment found in the health care provider's office for operation.

With the foregoing in mind, it is a primary object of the present invention to provide a novel apparatus and method which alleviate the problems of the prior art mentioned above.

An additional important object of the present invention is the provision of a multiple stage anti-microbial apparatus and related methods which significantly address the contamination and cross-contamination problems mentioned above.

An additional significant object of the present invention is to provide a novel method and unique apparatus by which a handpiece may be processed between successive uses on different patients to include soaking, removal of over-burden through use of ultrasonic energy, exposure to anti-microbial liquid, drying, exposing to anti-microbial heat, accommodating coordinated though separate autoclaving, and accommodating contiguously packaging of the handpiece in a heat shrunk sheath after multiple anti-microbial treatment to prevent later contamination through the air.

It is a further dominant object to provide a sheath which is heat shrunk upon a handpiece following anti-microbial treatment which accommodates manual severing thereof and removal prior to use on another patient.

It is a further paramount object to provide a novel handpiece sheath accommodating heat shrinking upon the handpiece and removal thereafter of a distal portion of the sheath only at the time of subsequent use along a weakened path to expose the operative head of the handpiece.

A further object of value is the provision of a heat shrinkable sheath with which a handpiece is encapsulated following anti-microbial treatment which accommodates grasping of the handpiece handle through a portion of the sheath during use of the handpiece and removal and discardation of the grasped portion of the sheath following use of the handpiece.

It is an additional object of the present invention to provide a novel anti-microbial apparatus which is relatively inexpensive, but efficacious.

An additional dominant object of the present invention is the provision of an anti-microbial apparatus which comprises a portable casing in which an ultrasonic basin and a heat chamber are carried.

A further principal object of the present invention is the provision of a novel anti-microbial apparatus comprising an ultrasonic basin which provides a bath for soaking, liquid anti-microbial activity, and removal of debris.

Another paramount object of the present invention is the provision of a novel anti-microbial apparatus comprising a heat chamber which accommodates facile manual introduction and movement therein of the distal end and a substantial portion of the handle of a handpiece following anti-microbial treatment.

An additional valuable object of the present invention is the provision of an anti-microbial apparatus comprising a heat chamber accommodating facile manual introduction and movement therein of the distal end and a substantial portion of the handle of a handpiece after the handpiece is placed in a heat shrinkable plastic to heat shrink the sheath as an anti-contamination measure.

A further important object of the present invention is the provision of an anti-microbial apparatus which is without water and drain connections and operates using household electricity.

A further primary object of the present invention is to provide a novel anti-microbial apparatus and related methods for use on most hand held medical instruments including but not limited to dental handpieces.

These and other objects and features of the present invention will be apparent from the detailed description taken with reference to the accompanying drawings.

DETAILED DESCRIPTION OF THE ILLUSTRATED EMBODIMENT

The Illustrated Apparatus

Reference is now made to the drawings, wherein like numerals are used to designate like parts throughout. Attention is particularly directed to FIGS. 1 through 10 which illustrate one anti-microbial apparatus, generally designated 20, fashioned in accordance with the principles of the present invention.

Figure 2:
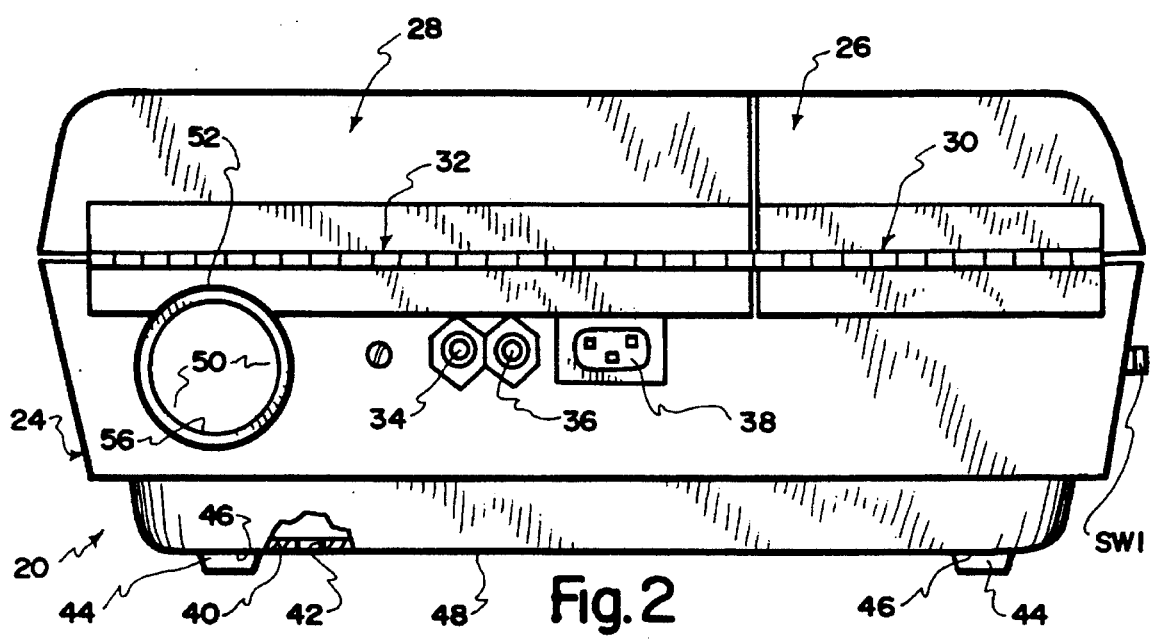
FIG. 2 is an enlarged rear elevation of the anti-microbial apparatus of FIG. 1 with an exhaust baffle removed for clarity of illustration.

Broadly, the present invention comprises a portable device encased within a common housing, generally designated 22. Housing 22 comprises a one-piece base or receptacle, generally designated 24, formed of a satisfactory strong shape-retaining synthetic resinous material. The housing 22 comprises two housing lids or covers, respectively generally designated 26 and 28. Each cover 26 and 28 is secured to the base 24 by a hinge, respectively generally designated 30 and 32 (FIG. 2). The cabinet comprising the base 24 and covers 26 and 28 is of a modified clamshell design, providing a compact, lightweight, and yet effective anti-microbial apparatus, the outside dimensions of which may comprise 12 inches from front-to-back, 13 inches from side-to-side, and 6½ vertical inches. The base 24 and lids 26 and 28 are preferably thermo molded of durable, di-electric easy-to-clean, high stain-resistant ABS plastic.

Exposed beyond the base 24 is a rocker actuator for a master off/on main power switch SW1 (located at one side of the base 24) and a panel 25 of membrane switches SW2, SW3, and SW4 for, respectively, enabling an ultrasonic circuit, generating anti-microbial heat at a heat applying site, and generating heat for heat shrinkage of sheath upon a handpiece following anti-microbial treatment. At the rear of the base 24 are reset buttons for circuit breakers 34 and 36 by which five amp and 15 amp circuit breakers may be, respectively, reset, as explained herein in greater detail. An electrical socket 38 is adjacent to the reset buttons for located circuit breakers 34 and 36. The electrical receptacle 38 is a 112 volt 15 amp AC electrical receptacle.

As best seen in FIG. 2, electrical socket 38 conventionally comprises three male connectors for engagement with the female end of a conventional electrical cord (not shown), the male end of which is connected to a source of 110 volt AC electrical power, such as is readily available in homes and commercial buildings.

The base 24 and the two exterior covers 26 and 28 are shells and comprise a relatively thin wall. See, for example, wall 40 illustrated in FIG. 2. Wall 40 comprises the bottom wall portion of the base 24. A plurality of apertures 42 are placed in the bottom wall portion 40, only one of which is illustrated in FIG. 2, for the purpose of accommodating atmospheric or ambient air flow through the base 24 to cool the circuitry and other components of the apparatus 20 during use.

The base 24 is supported upon four conventional elastomeric pedestals or non-slip feet 44, each of which is adhesively secured at interface 46 to the exterior surface 48 of the bottom wall 40. See FIGS. 2 and 3. The lightweight construction of the apparatus 20, including but not limited to the base 24 and covers 26 and 28, allow convenient portability, independent of the size, strength, and gender of the person assigned to move the apparatus 20 from place-to-place.

The apparatus 20 comprises a continuously open heating chamber 50. Heating chamber 50 is defined by a glazed, ceramic tube 52, illustrated as comprising inside and outside diameters, respectively, of uniform size throughout the length of the tube 50. Thus, the uniform wall thickness of tube 52 is constant. The tube 52 comprises an entry opening 54 and an exit or exhaust opening 56. Exhaust opening 56 is best illustrated in FIG. 2, where exhaust baffle 55 has been removed for clarity.

Figure 1:
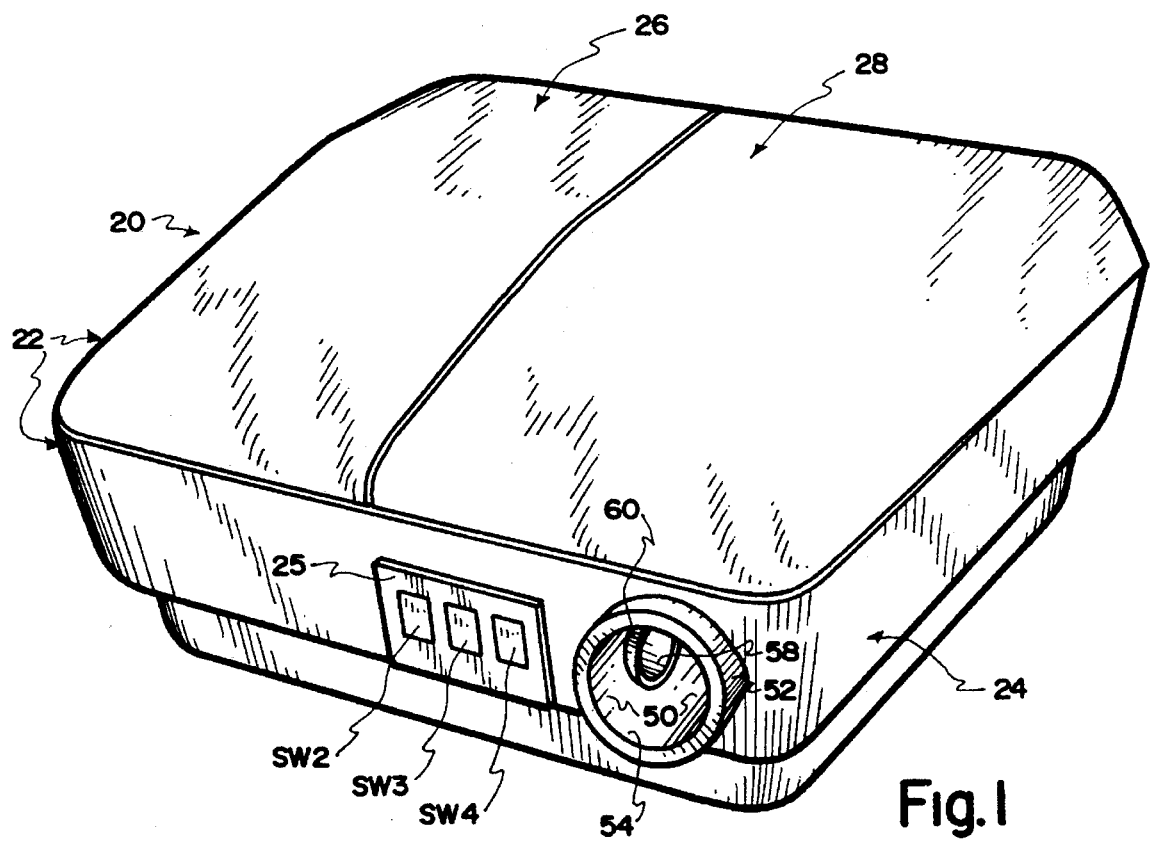
FIG. 1 is a perspective representation of an anti-microbial apparatus embodying the principles of the present invention.
Figure 4:
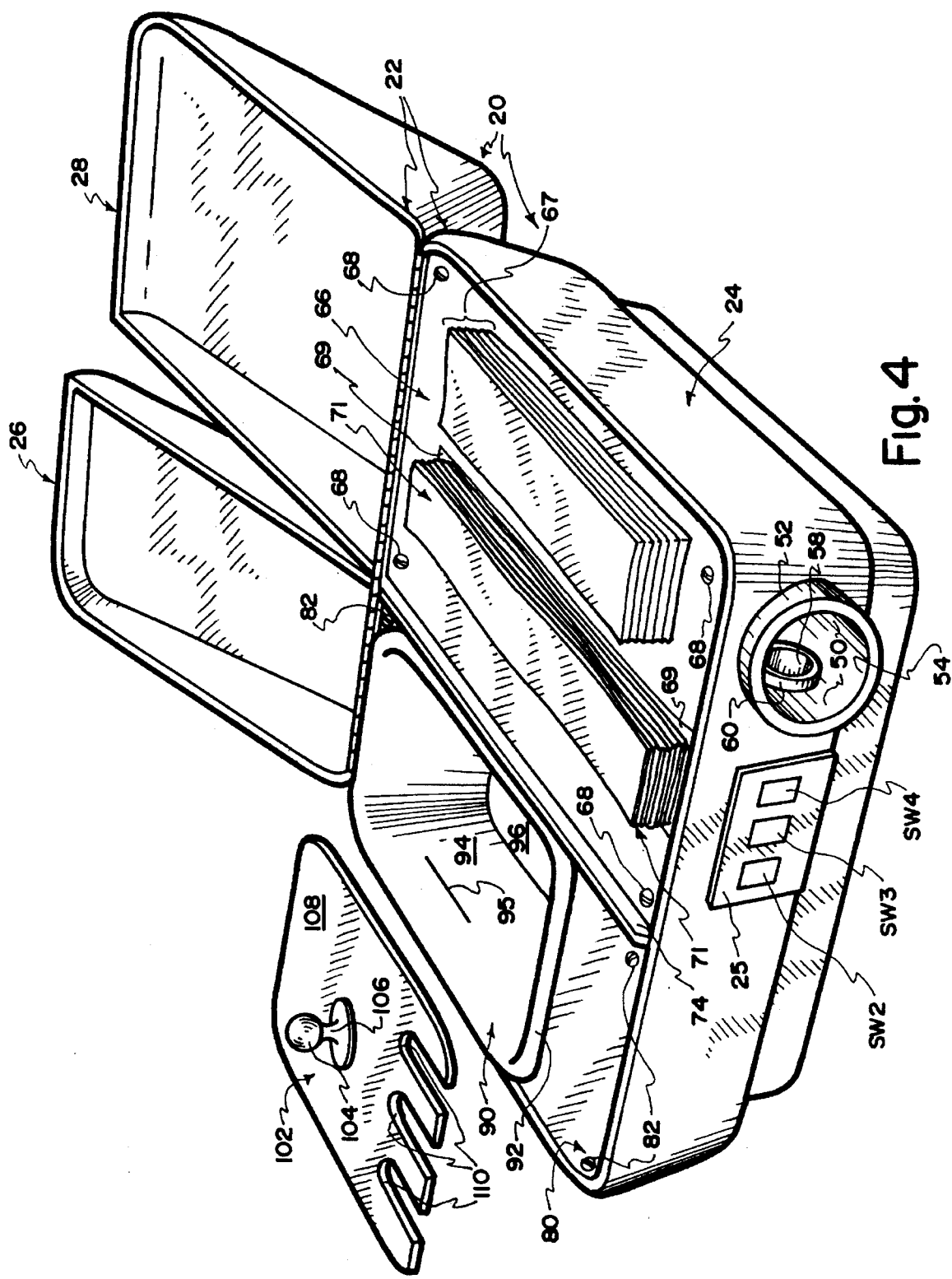
FIG. 4 is a perspective representation, partially exploded, of the anti-microbial apparatus of FIG. 1 showing the two lid segments pivoted into open positions.
Figure 7:
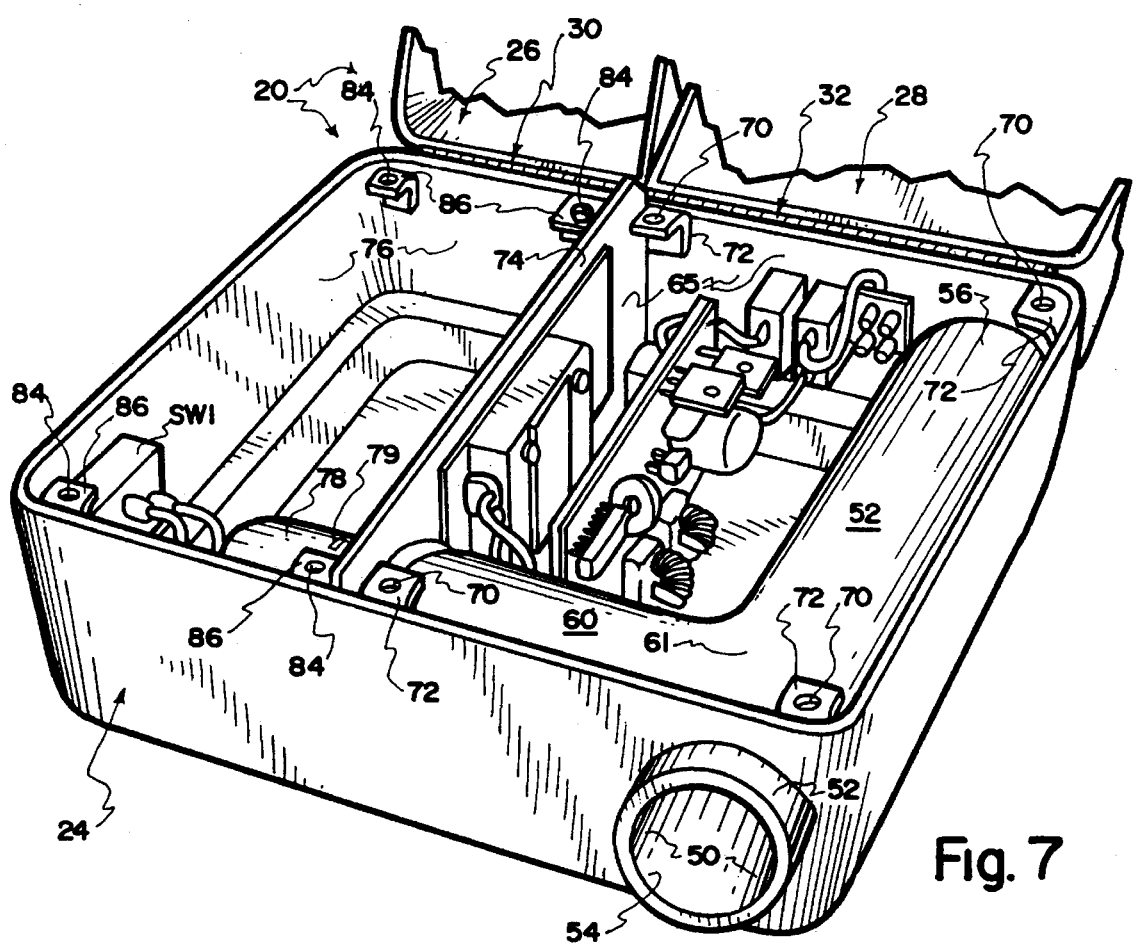
FIG. 7 is an enlarged perspective representation of the anti-microbial apparatus of FIG. 1 with the two covers open and the internal circuitry and heat conduits exposed to view.

As shown in FIGS. 1, 4, and 7, the heating chamber tube 52 is in communication with the discharge end 58 of a hot air supply tube 60. As can be seen from FIG. 4, heating chamber tube 52 and hot air supply tube 60 are disposed vertically below cover 28 when it is closed. A removable platform 66 is superimposed over tubes 52 and 60, as well as over the other interior components, particularly circuitry, disposed below the lid 28. The platform 66 is generally planar and comprises corner apertures through which screws 68 extend. The threads of screws 68 also engage, respectively, threaded apertures 70 in plastic brackets 72. See FIG. 7. L-shaped brackets 72 are secured to the associated wall surface base 24 using a suitable adhesive or any other desired conventional form of attachment. By removing screws 68, the platform 66 may be lifted from base 24 to accommodate inspection of and repairs within the compartment 65 below the platform 66 within the base 24.

As can best be seen in FIG. 7, the interior of the base 24 is compartmentized into two compartments by vertical wall 74, i.e., the above-described compartment 65 within the base 24 below platform 66 and a second compartment 76 directly below the exterior lid or cover 26 when closed. The compartment 76 is largely hollow, for reasons yet to be explained, but accommodates switch SW1 and placement of fan or blower 78.

Compartment 76 is only partially closed by a platform 80 (FIG. 4). Platform 80 is secured by removable screws 82 passing through corner apertures in the platform 80 into threaded bores 84 (FIG. 7) in the upper horizontal leg of L-shaped brackets 86. Each bracket 86 is secured to the associated interior surface of the wall comprising base 24 in any suitable fashion, such as by use of a suitable adhesive or bonding compound. Thus, platform 80 may be removed by unthreading screws 86 and, when removed, exposes the compartment 76. See FIG. 7.

Platform 80 comprises a relatively large aperture, located, sized, and shaped to accommodate gravity recessed placement of a stainless steel basin, generally designated 90. The basin 90 has a rolled peripheral edge 92 and a rectangularly-shaped tapered side wall 94 which merges with a flat bottom wall 96. The size and shape of basin 90 is selected so as to provide an appropriate liquid bath of predetermined acceptable volume for cleaning and anti-microbial treatment of medical/dental handpieces, as explained hereinafter in greater detail. Since the basin 90 simply rests at lip 92 upon the top surface of platform 90, the basin 90 can be lifted, as desired, to accommodate removal of the platform 80 and/or access to compartment 76. The basin or tank 90 may comprise a 16 or 22-gauge 302 stainless steel stamped and drawn tank comprising a width at lip 92 of 4½ inches, a length at lip 92 of 8.375 inches, and a 3-inch depth. The tank 90 is designed to operate with one liter of cleaning/disinfecting solution filled to an inscribed line 95 (FIG. 4).

Figure 6:
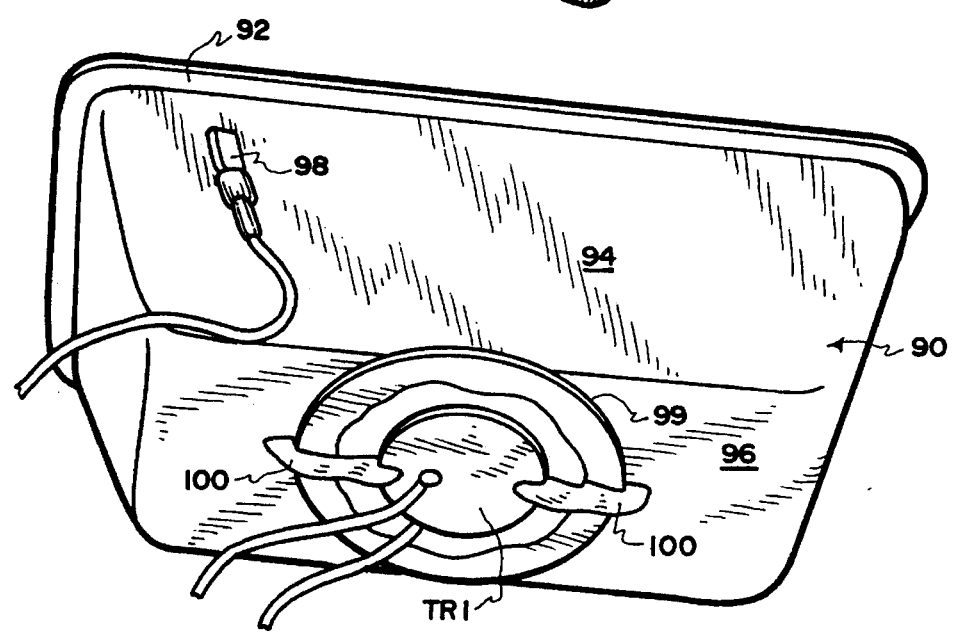
FIG. 6 is a bottom exploded perspective representation of the basin of FIG. 5, removed from the remainder of the apparatus of FIG. 1.

As best illustrated in FIG. 6, the stainless steel basin 90 is grounded at terminal 98 (FIG. 6), which is located in electrical communication with a side wall 94 of the basin 90 by soldering and pliant anchors 100. An ultrasonic transducer TR1 is yieldingly secured to the bottom 96 of the basin 90. While any suitable form of attachment may be used, the attachments 99 and 100 illustrated in FIG. 6 may comprise baked-on epoxy and silicone rubber, respectively.

Figure 5:
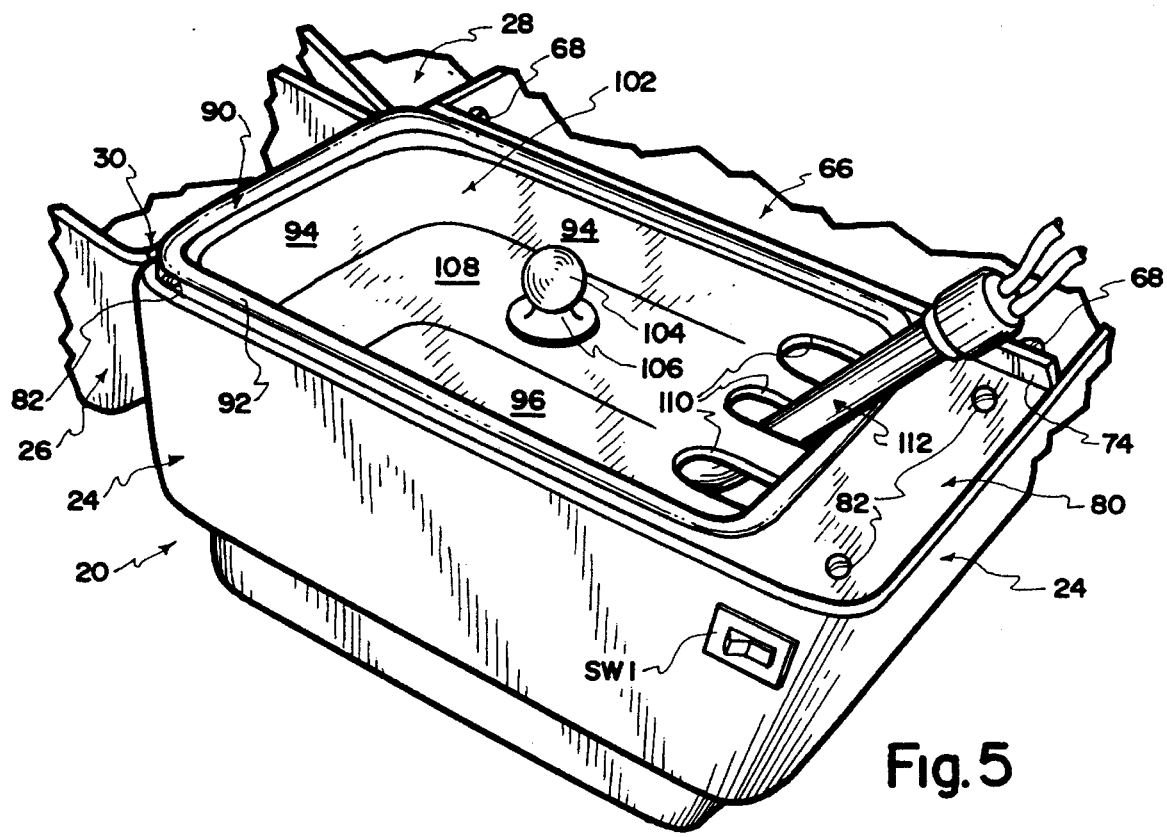
FIG. 5 is an enlarged fragmentary perspective of the left portion of the anti-microbial apparatus of FIG. 1, with the removable slotted lid positioned over the bath-forming basin of the apparatus.

A transparent, removable plastic basin lid 102 is selectively positioned, as illustrated in FIG. 5, over a liquid bath placed in basin 90, for purposes yet to be explained. The plastic lid 102 is substantially rectangular in its configuration, but slightly smaller dimensionally than the size of lip 92 of the basin 90 thereby accommodating interior or recessed placement, as illustrated in FIG. 5.

The plastic lid 102 comprises a knob 104 for manually manipulating the basin lid 102. Knob 104 is secured, as by bonding, gluing, or in any other suitable way at site 106 to or at the top surface 108 of basin lid 102. Basin lid 102 is illustrated as being substantially planar and of uniform thickness throughout. The perimeter comprises three edge slots 110, accommodating passage therethrough and upward extension therefrom of the proximal end of up to three handpieces 112, at any point in time, with the distal end and part of the handle of each such handpiece disposed within the bath of the basin 90, as illustrated in FIG. 5.

As best illustrated in FIG. 4, platform 66 accommodates placement of a stack or supply of paper towels 67. Adjacent thereto is a recess or well 69 into which a supply of handpiece heat shrinkage sheaths, each generally designated 71, is placed for periodic use, as hereinafter explained in greater detail.

Apparatus 20 is preferably lightweight, low cost, and easily operated with limited technical training by any health care provider, including technicians, nurses, doctors, and aids as well as dentists and doctors. Apparatus 20 is unconnected, except for electrical power in the illustrated embodiment, although the present invention contemplates a breadth such that a portable electrical power supply and liquid connections could be used. No drains and no water connections are involved in the illustrated embodiment.

The ceramic oven comprising tube 52 is small and always open accommodating a single hand held instrument. Flow therethrough from hot air supply tube 60 is laminar, the fan or blower 78 (FIG. 7) drawing air into the base 24 through holes 42, through influent fan or blower ports 79 across heat coils disposed in tube 60, into heating chamber tube 52. Blower 78 may be a motor and fan in combination and may be a Mabuchi RS285SA, 2073 DC motor connected to a medium pressure fan.

A second continuously running fan is preferably positioned below juncture 61 to exhaust hot air accumulated in compartment 65 through apertures 42. This fan is turned on and off upon actuation of the rocker actuator of the main power switch SW1. Tubes are suitably supported above bottom wall 40 to accommodate the fan. This fan may be a mini Delta fan, such as Model DFD0412LL, or the equivalent, having 11–13.8 V DC and 0.05 amp rating. The ceramic oven, in the form of tube 52, as stated above is open at both ends, accommodating hand held placement for drying, exposure to anti-microbial heat, and heat shrinking procedures, yet to be explained herein in greater detail.

It is to be appreciated that the liquid bath within the basin 90 is removed, from time-to-time as appropriate, using equipment available in the hospital, medical and dental offices where the apparatus 20 may be located. For example, the dental oral suction system may be used. Such removal of the disinfecting liquid bath from the basin 90 provides the further benefit of disinfecting and cleaning the suction line, the collection bottle, and the suctioning system itself. Paper towels may be used to wipe residual liquid from the interior surface of the basin after the bath has been aspirated. A 5% hypochlorite or a 5% bleach solution may be used to wipe any iodine or other stains from the surface of the basin 90 and from surrounding regions.

The ceramic tubes 52 and 60 are preferably molded of the highest quality "dinnerware" grade porcelain, fired at 2,000 degrees fahrenheit, which is then glazed both inside and out with a "dinnerware" porcelain glaze and again fired at 2,000 degrees farenheit. The resulting porcelain tubes are highly di-electric, non-staining, good heat insulators, and very easy to clean and disinfect with minimal effort. It is preferred that the material comprising the connector 61 (FIG. 7) be a suitable high temperature ceramic sealant.

The apparatus 20 will be accompanied by a supply of medical or surgical gloves, to be used by each health-care provider in an appropriate manner. Housing comprising base 24 and lids 26 and 28 accommodate silk-screening by which various forms of information can be applied thereto.

The hot air delivery tube 60 contains heating coils through which air delivered through vents under the displacement force of the fan 78 flows. The amount of heat imparted to the flow of air by the heating coils may be selectively set, as hereinafter more fully explained.

Figure 8:
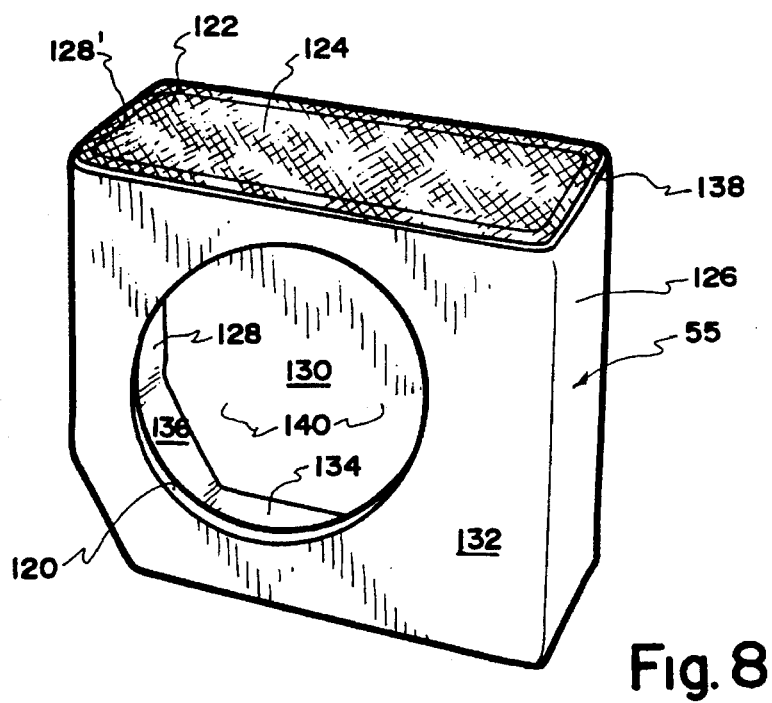
FIG. 8 is an enlarged perspective representation of the exhaust baffle shown to the right in FIG. 3.
Figure 3:
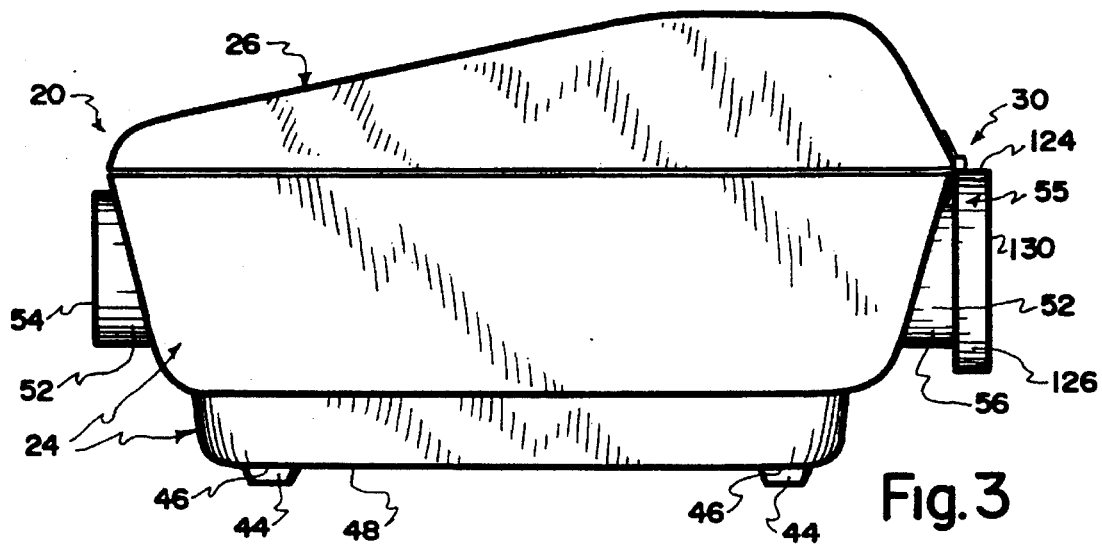
FIG. 3 is a side elevation of the anti-microbial apparatus of FIG. 1, with the exhaust baffle in place.

The exhaust baffle 55 is best illustrated in FIGS. 3 and 8. The exhaust baffle (which functions as air diverter and heat shield to prevent injury and damage) comprises a hollow box-shaped configuration comprising a circular air influent opening 120 and a rectangular effluent chimney opening 122, which is illustrated as being covered by a filter 124. See FIG. 8. The diameter of the circular influent opening 120 is sized so as to accommodate a manually removable press-fit union over the exposed discharge end 56 of the heating chamber tube 52. The user has the option of facilely utilizing the exhaust baffle 55 or not, as conditions may dictate.

The exhaust baffle 55 comprises solid informally thick side walls 126 and 128, a solid rear wall 130, each of uniform thickness, and formed as one piece. Baffle 55 also comprises a front wall 132 apertured at influent opening 120. Wall 132 is of uniform thickness and parallel to while offset from solid back wall 130. Wall 132 is integral with side walls 126 and 128. The exhaust baffle 55 also comprises a bottom wall 134, one piece with wall 132, of uniform thickness, disposed parallel to the plane containing exhaust opening 122. A short diagonal wall segment 136 joins as one piece side wall 128 and bottom wall 134. The upper edge 138 adjacent exhaust opening 122 is disposed within a horizontal plane. The filter 128' may be adhesively secured at its periphery to edge 138, the filter 128' functioning to cool the exhaust air, thereby reducing the temperature to a level well below that by which a human being may be injured.

The exhaust baffle 55 is preferably formed of a ceramic material which is temperature resistant and externally glazed to accommodate ease of cleaning. It may be formed of the same ceramic material from which tubes 52 and 60 are formed to simplify manufacturing. It is preferred that the volume within the hollow interior 140 of the exhaust diverter 55 be large enough to slow the laminar flow of hot air issuing from tube 52 to allow a predetermined dwell time therein, thereby enhancing the cooling function performed by the exhaust baffle 55.

The base 24 and the lids 26 and 28 are illustrated as being contoured, the top and sides being tapered.

The paper towels 67 are folded.

The Sheath

Figure 9:
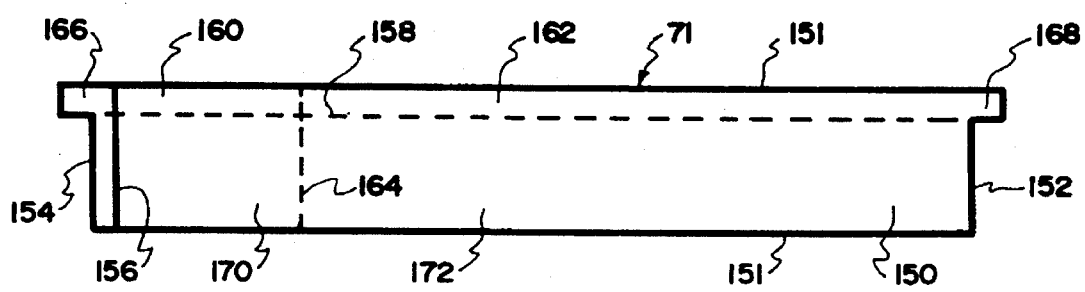
FIG. 9 is a plan view of a heat shrinkable sheath for encapsulation of a handpiece following anti-microbial treatment.
Figure 10:
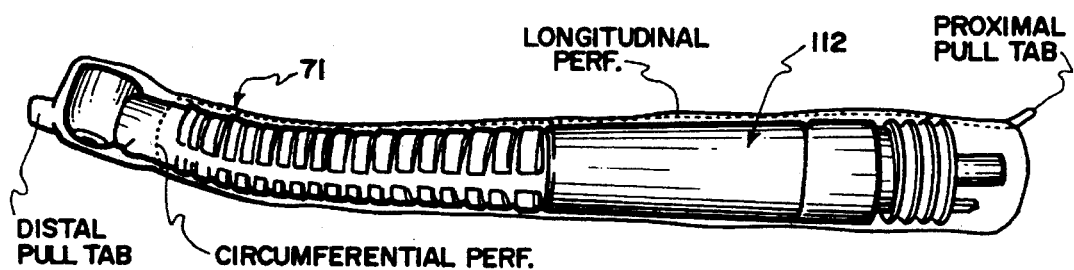
FIG. 10 is a perspective representation of a dental handpiece encapsulated by the sheath of FIG. 9 after the sheath has been heat shrunk.

Reference is now made to FIGS. 9 and 10 which illustrate one of the handpiece-receiving sheaths 71, shown in flat full-sized condition prior to and after being heat shrunk upon a handpiece 112, respectively. The sheath 71 comprises a thin-wall initially flat bag 150 of medical grade synthetic resinous material which is heat shrinkable with two pleats 151 for ease of storage. The bag or sleeve 150 is nevertheless illustrated as being longitudinally seamless along its entire length. The bag 150 is open for receipt of a handpiece at one end 152. End 154 of the sleeve or bag 150 is closed. While any suitable form of closure is satisfactory, in the illustrated embodiment end 154 is closed by a heat seal seam 156. As illustrated in FIG. 9, the bag 150 is shown in a collapsed, flat position.

The bag 150 comprises two longitudinally-directed weakened lines 158, in the form of spaced perforations, the perforations penetrating the wall comprising the bag 150 along two superimposed lines, the top line 158 being illustrated in FIG. 9. Thus, the bag 150 comprises a longitudinally directed edge ribbon comprising a distal ribbon portion 160 and a central and proximal ribbon portion 162. The two ribbon portions 160 and 162 are aligned one with the other. The two ribbon portions 160 and 162 are, prior to use, subdivided one from the other by a circumferential or transversely disposed weakened line 164 comprising spaced perforations which penetrate the wall comprising the bag 150 around the full 360 degree circumference of the bag. The aligned longitudinally directed ribbon portions 160 and 162 respectively terminate in a distal tab 166 and a proximal tab 168.

As explained herein in greater detail, the tab 166 accommodates manual grasping and tearing longitudinally along the perforations 160 to transverse perforations 164 and thence transversely along perforations or weakened line 164 to remove ribbon portion 160 and bag or sleeve segment 170 from the handpiece, after the bag has been heat shrunk thereon. This accommodates exposure of the distal end of the handpiece for placement of a burr or other such structure, while continuing to sheath the handle portion of the handpiece still encapsulated by sheath segment 172. This prevents communication of contamination from the hands or gloves of the instrument user to the handle of the handpiece and vice versa.

When use of the handpiece is over and the handpiece is ready for anti-microbial treatment, the remaining segment 172 of the bag 150 is removed by grasping tab 168 and pulling it along weakened line 158 to the end of bag segment 172, following which the bag segment 172 and the ribbon 162 are discarded.

The heat shrinkable material from which the sheath 71 is fabricated may be 1.25 mil., 60% shrink tubing formed of medical grade polyvinylchloride if desired. One or both of the sheath segments 170 and 172 may be color coded. For example, segment 170 may comprise a blue pigment, with segment 172 transparent, to facilitate visual identification of the location of transverse tear line 164 and to provide visual certainty as to the portion of the bag 150 to be removed to expose the distal end of the handpiece. The bag, once positioned and heat shrunk upon the handpiece, and prior to removal of any portion thereof, provides for open atmospherically or ambiently exposed storage following anti-microbial treatment wherein the handpiece is not subjected to air contamination while being so stored.

The disposable heat shrink tube sheath 71, with proximal and distal pull tabs aligned with longitudinal perforations 158, provides an inexpensive and yet effective disposable protection for medical and dental instruments which have been subjected to anti-microbial treatment and a convenient way for hospital, dental offices, and medical offices to non-contaminately handle such instruments conveniently and without extensive technical training or significant risks to the patient. Thus, the heat shrunk sheath 71 upon an instrument or handpiece provides a barrier which reduces or eliminates deposition of aerosol fall-out contamination on the handpiece. During use, the heat shrunk sheath 71 resists and reduces transmittal of contamination between the handpiece and the user. The shrunken nature of the sheath 71, with bag segment 172 remaining on the handpiece is skin-tight and, therefore, does not alter the tactile feel or control of the handpiece, as used by the health-care provider.

The Process

The apparatus 20 is capable of being hand carried to the desired location in a hospital, dental office, or medical office and placed upon an appropriate flat surface, such as a countertop. A conventional electrical cord, at one end, is plugged into a wall socket and attached to the electrical receptacle 38 of the apparatus 20 at the other end.

The outside hinged lid 26 is moved from its closed clamshell position (FIG. 1) to an open position (FIG. 4) and the basin cover 102 is removed from within the basin 90.

A suitable diluted disinfecting solution is placed in the basin 90 up to the inscribed line 95 to provide the proper volume of anti-microbial liquid comprises a bath contained within the basin 90.

Any number of disinfectants may be used in a proper diluted form to comprise the bath within the basin 90. For example, iodophor/nonoxynol-9 marketed as "Multi-Wash" by Gull Laboratories, Inc. of Salt Lake City, Utah, which is an anhydrous liquid mixture consisting chiefly of monononylphenyl ethers of polyethylene glycols in complex with iodine, may be used. Any suitable EPA registered disinfectant may be used.

To the extent advisable, the distal end and the part of the handle earlier immersed within the bath contained in basin 9 are subjected to rinsing, by any suitable liquid, such as distilled water. Only some disinfectants require a rinsing cycle following removal from the bath. Others do not. Iodophor/nonoxynol-9 (Multi-Wash) requires no rinse.

One way of providing a suitable, easily handled system for dilution of a concentrated disinfectant is to provide a predetermined amount of concentrated disinfectant in a small container, adequate to provide an appropriate diluted quantity when mixed with one gallon of distilled or other suitable water. By providing a gallon container of suitable water, with sufficient air volume at the top to receive all of the concentrated disinfectant from the smaller container, the contents of the smaller container are simply poured into the large container, which is then recapped and oscillated until a uniform mixture is obtained. From the diluted disinfectant in the one gallon container, the basin 90 may be filled more than once. Where the iodophor/nonoxynol-9 disinfectant is used, and 1.2 fluid ounces of the Multi-Wash concentrate is added to one gallon of distilled water, the result is a a-(p-Nonylphenyl)-w hydroxpoly-(oxyethylene)-Iodine complex of 150 ppm Iodine dilution.

While distilled water is preferred, the iodophor/nonoxynol-9 diluted solution mentioned above is unaffected by water hardness up to at least 150 ppm $CaCO_3$ and, therefore, can be diluted in tap water.

It is recommended that the resulting diluted solution be allowed to set in the basin 90 for a time sufficient to warm to room temperature and to de-aerate, which may take approximately one hour before the bath within the basin 90 should be used initially.

Periodically, the anti-microbial value of the bath within the basin 90 should be checked. A pHydrion micro-IODINE test tape may be used. This product is available from Micro Essential Laboratory of Brooklyn, N.Y.

Once the sanitizing liquid comprising the bath within basin 90 is ready for use, the soiled distal end of a medical instrument, such as a dental handpiece 71, and part of the handle thereof is placed in the bath, as illustrated in FIG. 5. While not mandatory, the air and water tubes associated with operation of the handpiece 112 may be left in their connected condition as the distal end and part of the handle of the handpiece 112 is allowed to soak. This type of soaking after use prevents the overburden or debris on the instrument from drying, among other things.

With at least one handpiece 112 in its soaking position as illustrated in FIG. 5, the operator actuates the main power switch SW1 to communicate electrical energy to the circuits of the apparatus 20, which circuits are yet to be described. Thereafter, the operator of the apparatus 20, with a used handpiece 112 soaking in the bath of basin 90, actuates the membrane switch SW2 which delivers electrical energy to the ultrasonic transducer TR1 (FIG. 6), thereby dissipating ultrasonic energy or waves through the bath and across the instrument 112. By subjecting the bath and the handpiece 112 to ultrasonic waves causes the debris or overburden to be removed from the handpiece 112 and assists the disinfectant within the bath to reach most if not all surface areas of the portion of the handpiece 112 immersed within the bath. While not mandatory in accordance with the principles of the present invention, a timing circuit is provided which limits the length of time to which the bath and the handpiece 112 are subjected to the ultrasonic energy emitted by transducer TR1.

Caution should be taken so that the ultrasound transducer is not operated when the basin 90 is empty.

If the potency of the diluted disinfectant within basin 90 falls below a predetermined amount, the bath should be aspirated, and appropriately replaced, as explained above.

When the soaking, anti-microbial bathing, and ultrasonic steps have been completed, the basin lid 102 is lifted and the handpiece 112 removed, after which the lid 102 is returned to its in-basin position.

It is always advisable to actuate the handpiece after being removed from the bath contained within basin 90 so as to drive air and liquid cleaning solution through the handpiece from the supply hoses attached at the proximal thereof. The air/water discharge may be directed into a towel to prevent discharge of airborne pollution. This will remove any residual debris and other sources of contamination as well as bath solution from the interior passageways at the distal end of the handpiece 112.

In any event, after removal from the bath where no rinsing is required or after rinsing where required, a paper towel is preferably removed from the stack 67 of towels and the handpiece is lightly tapped against and air and water operated into the towel, preferably while held in one hand of the operator. The towel may also be used to remove surface liquid from the handpiece.

Holding the handpiece 112 in one hand, the operator next inserts substantially all, except for the proximal end being held in the hand, into the anti-microbial heat chamber 50 and actuates membrane switch SW3. Anti-microbial heat, at an appropriate temperature of typically 750 degrees fahrenheit or more, is delivered from the heating coils contained within tube 60, by operation of the fan 78, resulting in laminar flow through the interior of the tube 52, which both dries residual liquid on the handpiece 112 and subjects the handpiece to anti-microbial heat. A temperature of about 750 degrees farenheit or higher is appropriate. Normally a timed interval of about 15 seconds is satisfactory, although greater lengths of time could be used to enhance the anti-microbial effectiveness. Repeat anti-microbial heat cycles may also be used. However, care should be taken to avoid heat damage to the handpiece. The capacity to harmlessly absorb heat varies from handpiece to handpiece. It is preferred that the circuitry of the apparatus 20 comprise a predetermined cycle time for drying and anti-microbial heat exposure, during which time it is recommended that the operator moderately rotate and/or otherwise move the handpiece while it is extended into the tube 52.

In situations where the anti-microbial heat available by reason of one or more cycles of exposure of the handpiece 112 to anti-microbial heat in chamber 50 is deemed insufficient, the air and water hoses may be removed from the handpiece 112 and the handpiece can be subjected to autoclaving.

The fingers of the operator are not to be inserted into the ultrasound tank nor into the ceramic tube 52 during operation.

After removal of the handpiece 112 from the anti-microbial heat chamber 50 or, in the alternative, after autoclaving where autoclaving is used, the anti-microbially treated handpiece is placed through the open distal end 152 of one of the sheaths 71. While the handpiece may be inserted up to seam 156, it is preferred presently that the handpiece be left spaced a short distance from the seam 156 to accommodate shrinkage.

The sheathed handpiece is next manually placed within and manually held within the chamber 50 defined by tube 52. The heat shrink switch SW4 is actuated and the sheathed handpiece rotated and/or otherwise moved moderately within the chamber 50 as the sheath is heat shrunk. The actuation of switch SW4 subjects the sheath to a heat shrinking temperature of approximately 450 degrees fahrenheit for an interval of approximately twelve or more seconds. If desired, a suitable lubricant can be applied to the handpiece prior to placement in the sheath 71 or after removal of sheath segment 170.

When the heat shrinking cycle is over, the encapsulated handpiece is manually removed from the chamber 50 with the sheath shrunk into snug contiguous conforming relation with the handpiece. When use of the apparatus 20 has been completed, the main power switch SW1 is shut off at its rocker actuator exposed at the left side of the base 24. The closed distal end 154 shrouds the distal end of the handpiece. While it is preferred that the length of the sheath 71 be such as to cover the distal end and the entire handle of the handpiece, the present invention is broad enough to include coverage of the distal end only or the distal end and a part of the handle of the handpiece 112.

The contiguously encapsulated sheathed handpiece is thereafter stored in an open condition in a desired storage place in the hospital, the doctor's office, or the dental office. The contiguous sheath prevents air-borne contamination of the encapsulated handpiece.

At the time of use, the heath-care provider lifts the sheathed handpiece from its storage location and, if not already connected, the air and water hoses are connected at the proximal end of the handpiece.

The distal segment 170 of the heat shrunk sheath 71 is manually removed by grasping distal tab 166 and tearing first along weakened line 158 to weakened line 164 and thence along weakened line 164 away from line 158 until segment 170 has been severed from the handpiece. Segment 170 and ribbon portion 160 are then discarded. The burr or other distal workpiece instrumentation of the handpiece is added. The health-care provider grasps the handle of the handpiece through the heat shrunk sheath segment 172 as the handpiece is used with the patient.

When use of the handpiece has been completed, the distal tab 168 is manually grasped and the sheath segment 172 is removed by tearing the ribbon 162 from the sheath segment 172 along weakened line 158. Both the ribbon 162 and the segment 172 are then discarded.

The handpiece is returned to its soaking position in the disinfecting bath contained within basin 90 and the process is repeated.

It is to be appreciated that the tool or instrumentation fixed during use to the distal end of the handpiece is normally removed after use and is separately cleansed and anti-microbially treated prior to subsequent use, or discarded if disposable.

Use of surgical or like gloves is recommended during both the use of the handpiece 112 and during handling of the handpiece as it is soaked, cleaned, and anti-microbial treated. Re-gloving is recommended when the gloves either become contaminated or are in some way damaged during use.

The Circuit Diagrams

Figure 11:
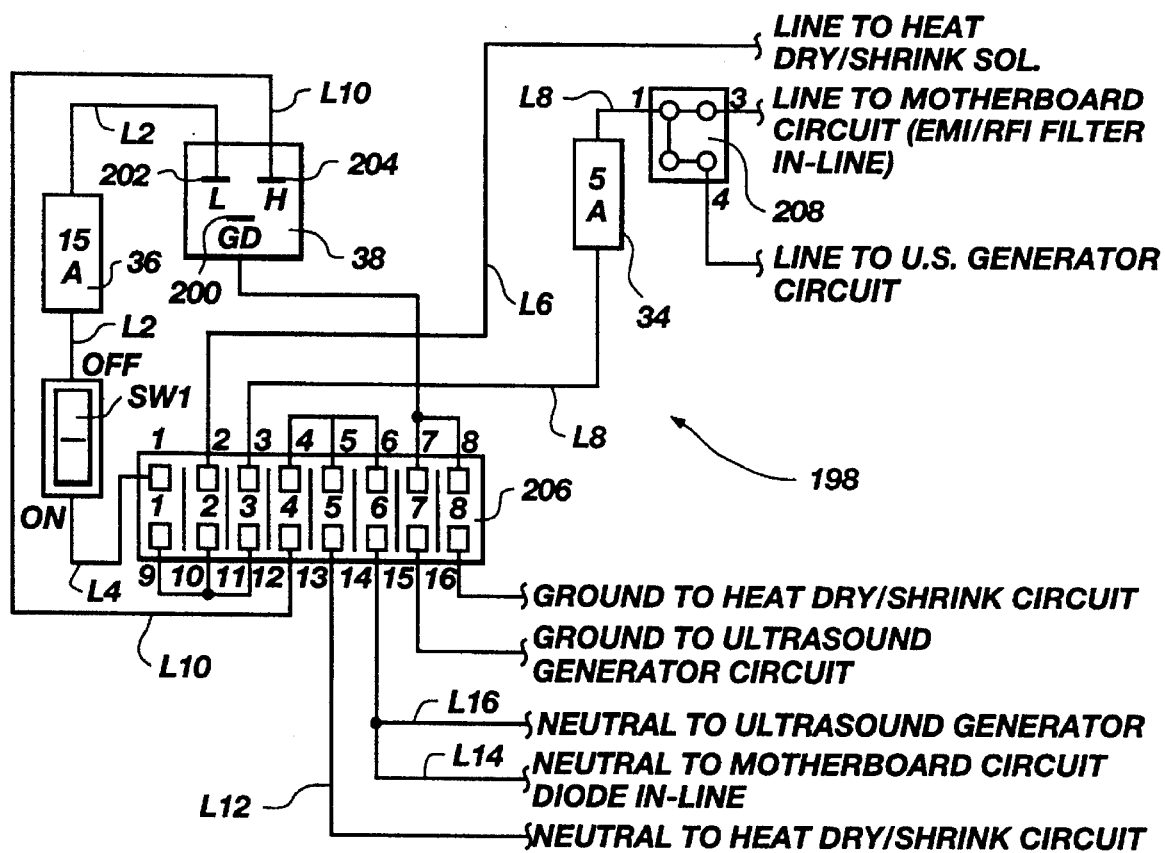
FIG. 11 is a main wiring diagram for the anti-microbial apparatus of FIG. 1.

Reference is now made to FIG. 11 which is the main wiring diagram by which electrical power is distributed to specific circuits comprising part of the apparatus 20. Conventional 110 v, 60 cycle AC electrical power is communicated, as mentioned above, to three pronged receptacle 38. One terminal 200 of receptacle 38 is at ground potential. Another terminal 204 is neutral, while terminal 202 is hot.

When the main power or master switch SW1 is off, the apparatus 20 is starved for power. When switch SW1 is manually displaced to its on position, power is communicated from terminal 202 of receptacle 38 along conductor L2, across 15 amp circuit breaker 36 and closed switch SW1 and along conductor L4 to terminal 1 of distribution strip 206. Circuit breaker 36 may be an E-T-A series 1658-P10 or equivalent. Terminal block or strip 206 may be a Wieland Euro-style eight-position terminal block. The power input at terminal 1 of strip 206 is communicated across terminals 9, 10, 11, 2, and 3 of strip 206 to conductors L6 and L8. Conductor L6 supplies electrical power to the heating coils in tube 60. Power communicated along conductor L8 across 5 amp circuit breaker 34, which may also be an E-T-A series 1658-P10 or equivalent, to terminal 1 of distribution strip 208. This power is output from terminals 3 and 4 of strip 208 to the motherboard circuit and the ultrasonic circuits, respectively.

Terminal 204 of receptacle 38 is connected by conductor L10 to terminal 12 of strip 206, thereby placing terminals 4, 5, 6, 13, and 14 and conductors L12, L14, and L16 at neutral.

Ground terminal 200 of receptacle 38 is connected to and grounds terminals 7 and 8 of strip 206. The ground for the heating coils in tube 60 and the ground for the ultrasound circuit are respectively ground at terminals 16 and 15.

Figure 12:
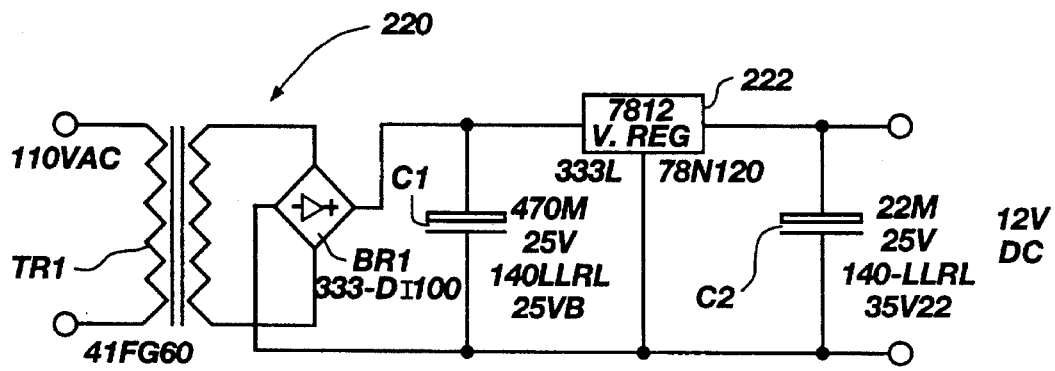
FIG. 12 illustrates a DC power circuit.

Reference is now made to FIG. 12, which illustrates the motherboard low voltage, DC power circuit, generally designated 220. Conventional 110 VAC power is tapped from the wiring diagram 198 of FIG. 11 and applied to the high voltage side of transformer TR1, which is a conventional 110 VAC to 12.6 VAC, 500 m amp transformer. The transformer TR1 thus provides a low 12.6 volts AC output to bridge rectifier BR1. Rectifier BR1 may be a 1 amp, 50 PIV rectifier, one side of which is at ground. The 12.6 volts DC output from rectifier BR1 is communicated to the 12 volt circuits, yet to be described, across fixed voltage regulator 222, which has a 12 V DC 1 amp output.

Element C1 is a 470 micro-farad capacitor which serves to flatten the 60 HzDC issuing from the AC transformer TR1 through the bridge rectifier R1 to the voltage regulator 222. The 22 microfarad capacitor C2 serves to flatten out and remove any high frequency noise which occurs in the +12 V DC power supply.

Figure 13:
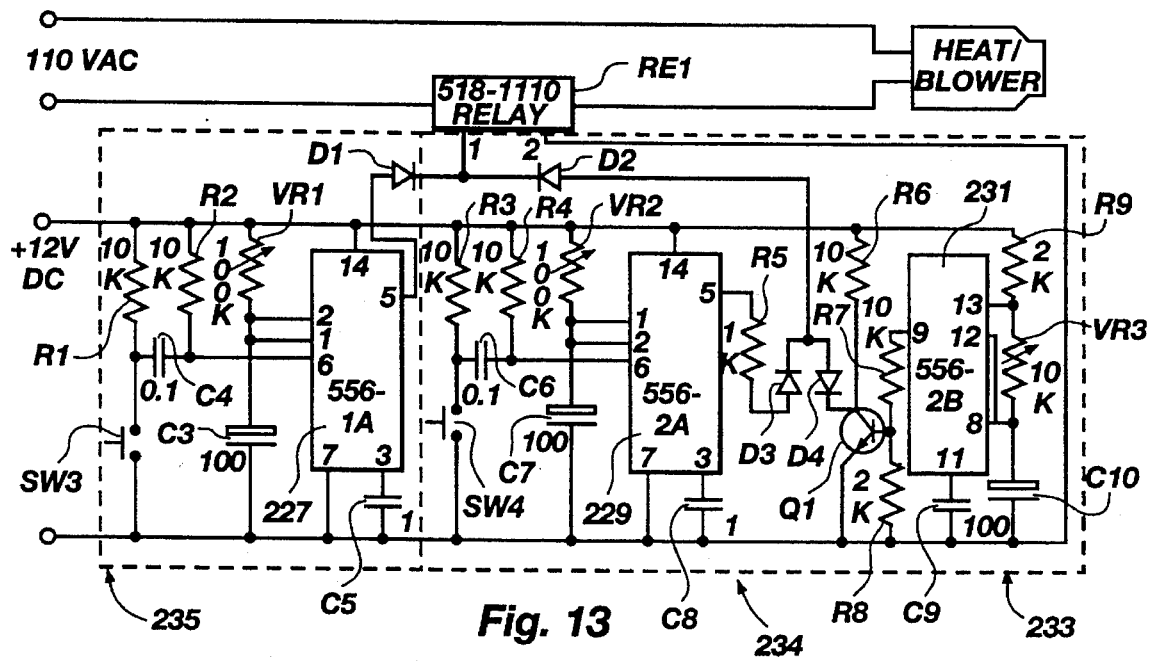
FIG. 13 is a heat/blower control circuit diagram.

Reference is now made to FIG. 13, which illustrates the heat/blower control circuit, generally designated 234. The 110 VAC power supply is communicated at one side to the fan 78 and the heating coils within tube 60 and at the other side to relay RE1. Relay RE1 is normally open, which starves the fan 78 and the heating coils for power until relay RE1 becomes conductive, as explained below.

The +12 V DC power supply is communicated to circuits 235 and 233, either of which can energize the coil of relay RE1. The positive end of the coil is connected to terminal 1 of relay RE1, while terminal 2 is at ground potential.

The +12 V DC power supply is connected directly to terminals 14 of integrated timing circuits 227 and 229 and across variable resistors VR1 and VR2 to terminals 1 and 2 of integrated circuits 227 and 229. The +12 V DC power supply is also connected respectively across resistors R2 and R4 to terminal 6 of circuits 227 and 229.

Terminal 7 of each of circuits 227 and 229 is at ground potential. Capacitors C5 and C8 respectively connect at one side thereof to terminal 3 of circuits 227 and 229, with the other side at ground.

Integrated circuits 227 is a first integrated circuit 236 (FIG. 14) which component may be part no. 511-HE556 available from Signetics. Integrated circuits 229 and 231 are first and second sections of the same component, which component may be part no. 511-HE556.

Capacitors C4, C3, and C5 each function to eliminate high and low frequency interference injected into the lines from switches, relays, and outside influences.

Resistors R1 and R2 function, respectively, to lower the amperage (to about 1 milliamp) to prolong life of the membrane switch and to reduce voltage to properly operate timer 227.

Circuit 235 is activated when switch SW3 is manually actuated. Variable resistor VR1 can be selectively set and functions, when circuit 235 is on, to initially deliver electrical power to terminals 1 and 2 of integrated circuit 227, which triggers circuit 227. The time sequence is lengthened by adjusting variable resistor VR1. Higher resistance yields longer time sequence (adjustable from 0 seconds to +1 hour).

After switch SW3 is on and circuit 227 is triggered, the output from circuit 227 at terminal 5 thereof across diode D1 energizes the coil of relay RE1 to a relatively high level thereby completing the circuit to fan 78 and the heating coils in tube 60. The temperature emanating from the heating coils is relatively high, on the order of 750° F. or more, thereby producing the above-mentioned anti-microbial heat in chamber 50. Production of this heat continues until timer 227 shuts off at the pre-set time lapse as adjusted and set by variable resistor VR1 during the assembly stage of the circuit. A fixed resistor of the appropriate value may be used in place of variable resistors VR1, VR2, and VR3, however, to do so does not allow fine-tuning the timing sequences.

Capacitors C6, C7, and C8 each functions to remove low frequency and high frequency noise injected by the operation of switches, relays, and even outside influence.

Resistors R3 and R4 function, respectively, to reduce amperage at SW4 to prolong membrane switch life and to reduce voltage to proper voltage for operation of timer 229.

Variable resistor VR2 can be selectively set and functions, when circuit 233 is on, to initially deliver electrical power to terminals 1 and 2 of integrated circuit 229, which triggers circuit 229. Variable resistor VR2 performs the same function as variable resistor VR1.

After switch SW4 is on and circuit 229 is triggered, the output from circuit 229 at terminal 5 thereof is across resistor R5 and diodes D3 and D2, which energizes the coil of relay RE1 to a relatively low level thereby completing the circuit to fan 78 and the heating coils in tube 60. The temperature emanating from the heating coils is relatively low, on the order of 450° F., thereby producing the above-mentioned heat shrink temperature in chamber 50. Production of this heat continues until timer 229 shuts off.

The output from terminal 5 of timer 229 is also communicated across diode D4 to the collector of transistor Q1. The +12 V DC power is also supplied across resistor R6. The base of transistor Q1 is made conductive by power supplied across resistor R7 from terminal 9 of timer 231. Once the transistor Q1 is conductive, it discharges to ground at the emitter thereof. This reduces the power level communicated to terminal 1 of relay RE1 from timer 229.

One side of capacitor C9 is connected to terminal 11 of timer 231, with the other side being at ground.

The +12 V DC power supply is communicated across resistor R9 to terminal 13 of timer 231 and thence across variable resistor VR3 to terminals 12 and 8 of timer 231, which terminals also connect to one side of capacitor C10, the other side of which is at ground.

Resistor R5 is current limiting and serves to reduce voltage to three volts, while resistor R6 functions in the same way.

The purpose of each of the resistors R7 and R8 is to reduce the voltage to less than one volt to be compatible with the transistor Q1.

Resistor R9 serves to divide the on and off time cycle for variable resistor V3 while variable resistor VR3 performs the function of controlling the division or percentage of power reaching related terminals of timer 231.

Diodes D1 and D2 function collectively as an OR gate. Diode D1 works when the anti-microbial heat cycle is on. Diode D2 works during the heat shrink cycle. Diodes D3 and D4 each serves to combine signals to control timer and power percentage.

Capacitors C9 and C10 respectively removes oscillation and, in conjunction with resistor R9 and variable resistor VR3 to control percentage of power.

Transistor Q1 is a phase converter.

Figure 14:
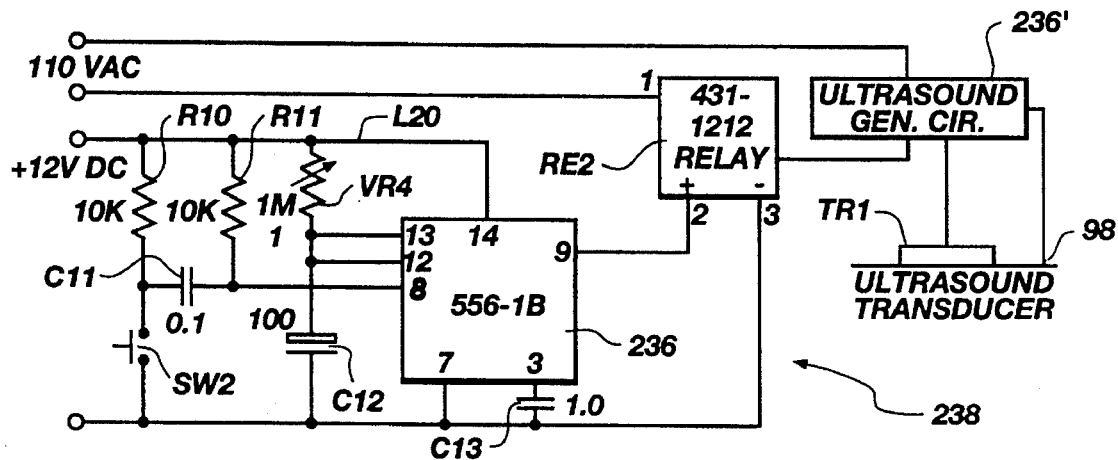
FIG. 14 is a diagram of an ultrasound timer circuit.

Reference is now made to FIG. 14, which illustrates an ultrasound timing circuit, generally designated 238. The 110 VAC power supply is communicated to circuit 238 so that hot conductor is connected to a conventional ultrasound generator circuit 236' and ground is connected to terminal 1 of relay RE2. Thus, relay RE2 functions as a switch and must be turned on before ultrasound generator circuit 236 is energized. When RE2 is turned on, ultrasound generator circuit 236 delivers power to transducer TR1 causing emission therefrom of ultrasonic vibrations as explained above. Relay RE2 may be a 100 V, 2 amp relay with a 12 v, 30 micro amp coil, such as part 431-1212. Circuit 236 may be a 556 DIP, 14 dual timer, part no. 511-NE-556.

The coil of relay RE2 is turned on by integrating timing component 236, terminal 9 of timer 236 being connected to the positive side of the coil at terminal 2 of relay RE2. The negative side of the coil, at terminal 3 of relay RE2, is at ground potential.

The +12 V DC power supply is communicated along conductor L20 to terminal 14 of timer 236, across fine tuning variable resistor VR4 to terminals 12 and 13 of timer 236 and across resistor R11 to terminal 8 of timer 236. Terminal 7 of timer 236 is at ground potential, while terminal 3 is connected to one side of capacitor C13, the other side of which is at ground potential.

The timer 236 is triggered upon manual closing of ultrasonic switch SW2 (with the main power switch SW1 on).

Resistor R10 serves to drop current (amperage to 1 milliamp) at switch SW2 to prolong the membrane switch cycle life, while resistor R11 functions to drop voltage to correct operating voltage supply to terminal 8 on timer 236.

Capacitor 12 serves to remove both low and high interference signals from the line caused by switches and other electronic devices, while the purpose of capacitor C13 is to remove both high and low frequency interference in ground line from relay RE2 and other outside influences.

Potentiometer or variable resistor VR4 is adjustable, the resistance of which increases with time so that at a predetermined time timer 236 is starved for power thereby turning relay RE2 off.

Figure 15:
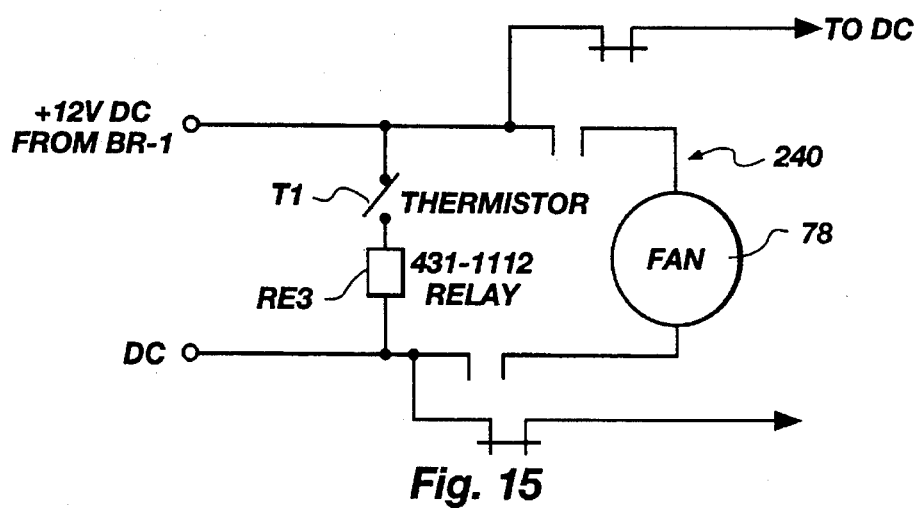
FIG. 15 is a diagram of an overheat control circuit.

Reference is now made to FIG. 15, which illustrates an over-heat control circuit, generally designated 240, preferably mounted on a motherboard. The +12 V DC power supply from circuit 220 is communicated to the input of circuit 240. Thermistor T1, located on the exterior of tube 52, is normally closed, but opens when the main power switch SW1 is on and either switch SW3 or SW4 has been actuated and the external temperature of tube 52 has reached a predetermined magnitude. Thermistor 71 may be a ¾" bimetal disk relay with an automatic reset feature.

Opening of thermistor T1 turns hot air fan or blower 78 on, thereby driving air from tube 60 through heating chamber tube 52.

Relay RE3 functions to open the 12 V DC lines to shut down communication of the DC power to the relays RE1 and RE2 (see FIGS. 13 and 14), and closes the line to fan 78 until such time as the temperature in the compartment 65 falls below 130° F. When the temperature in compartment 65 falls below 130°F., the Thermistor T1 automatically resets, which shuts down and re-closes the circuit by which DC power is provided.

The invention may be embodied in other specific forms without departing from the spirit or essential characteristics thereof. The present embodiment is, therefore, to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. In combination, an unattached medical or dental handpiece and an anti-contamination collapsible sheath, the handpiece comprising an exterior surface, a distal work-performing end, and a proximal end;

the sheath being contiguously shrunk upon the exterior surface of the handpiece and comprising a closed distal end portion and a second portion disposed proximal of the distal end portion, the distal end portion being connected to the second portion at a circumferential tear line accommodating manual detachment along the circumferential tear line of the distal end portion and removal of the distal end portion from the handpiece thereby exposing the work-performing end of the handpiece, leaving the second portion contiguous with the handpiece for grasping the handpiece through the second portion.

2. The combination of claim 1 wherein the distal end portion of the sheath comprises a pull tab formed as one piece with the sheath to enhance separation of the distal end portion from the second portion.

3. The combination of claim 1 wherein the second portion of the sheath comprises at least one longitudinally-directed tear line for removal of the second portion when use of the handpiece on the patient has been completed.

4. The combination of claim 3 wherein the second portion comprises a pull tab formed as one piece with the sheath to enhance separation of the longitudinal tear line.

5. The combination of claim 1 wherein at least a portion of the sheath comprises transparent synthetic resinous material.

6. The combination according to claim 1 wherein the sheath comprises two spaced crease lines accommodating storage of the sheath prior to use in a flat condition.

* * * * *